US008499721B2

(12) United States Patent
Gorans et al.

(10) Patent No.: US 8,499,721 B2
(45) Date of Patent: Aug. 6, 2013

(54) APPARATUS AND METHOD FOR NASAL DELIVERY OF COMPOSITIONS TO BIRDS

(75) Inventors: Marc S. Gorans, Willmar, MN (US); Matthew H. Erickson, Raymond, MN (US)

(73) Assignee: Nova-Tech Engineering, Inc., Willmar, MN (US)

( * ) Notice: Subject to any disclaimer, the term of this patent is extended or adjusted under 35 U.S.C. 154(b) by 2017 days.

(21) Appl. No.: 10/702,988

(22) Filed: Nov. 6, 2003

(65) Prior Publication Data

US 2005/0101937 A1 May 12, 2005

(51) Int. Cl.
*A01K 15/04* (2006.01)
*A61B 18/04* (2006.01)

(52) U.S. Cl.
USPC .......................................... 119/837; 606/164

(58) Field of Classification Search
USPC ................ 119/650, 651, 652, 655, 660, 661, 119/662, 665, 667, 669, 676, 713, 837, 843; 606/164
See application file for complete search history.

(56) References Cited

U.S. PATENT DOCUMENTS

| | | | | | |
|---|---|---|---|---|---|
| 2,434,875 | A | * | 1/1948 | Turnbull et al. | 604/207 |
| 3,295,524 | A | * | 1/1967 | Parker | 604/46 |
| 3,502,079 | A | * | 3/1970 | Simmons et al. | 128/200.14 |
| 3,570,487 | A | * | 3/1971 | Reynolds | 604/20 |
| 3,641,998 | A | * | 2/1972 | Lyon et al. | 604/152 |
| 3,859,996 | A | * | 1/1975 | Mizzy et al. | 604/70 |
| 3,874,381 | A | * | 4/1975 | Baum | 128/200.14 |
| 3,937,440 | A | | 2/1976 | MacGregor et al. | |
| 4,177,810 | A | | 12/1979 | Gourlandt | |
| 4,316,464 | A | * | 2/1982 | Peterson | 604/24 |
| 4,343,310 | A | * | 8/1982 | DuBose et al. | 606/164 |
| 4,375,814 | A | | 3/1983 | Gourlandt | |
| 4,381,773 | A | * | 5/1983 | Goodnow et al. | 128/200.14 |
| 4,417,663 | A | | 11/1983 | Suzuki | |
| 4,446,819 | A | | 5/1984 | Gourlandt | |
| 4,449,968 | A | | 5/1984 | Peterson | |
| 4,650,469 | A | | 3/1987 | Berg et al. | |
| 4,653,719 | A | | 3/1987 | Cabrera et al. | |
| 4,681,565 | A | | 7/1987 | Gourlandt | |
| 4,715,786 | A | | 12/1987 | Wolff et al. | |
| 4,850,997 | A | | 7/1989 | DuBose | |
| 4,863,443 | A | | 9/1989 | Hornung | |
| 4,951,610 | A | | 8/1990 | Gourlandt | |
| 5,195,925 | A | | 3/1993 | Gorans et al. | |

(Continued)

FOREIGN PATENT DOCUMENTS

| | | | |
|---|---|---|---|
| FR | 2 808 671 | | 11/2001 |
| FR | 2808671 | * | 11/2001 |
| FR | 2 839 245 | | 11/2003 |
| FR | 2839245 | * | 11/2003 |

*Primary Examiner* — David Parsley

(74) *Attorney, Agent, or Firm* — Mueting, Raasch & Gebhardt, P.A.

(57) ABSTRACT

Apparatus and methods for delivering a composition to a bird. A selected dosage of the composition may be delivered directly to one or both nostrils of the bird. The deliveries are performed through one or two fluid passages that are preferably in direct fluid communication with the birds' nostrils. Delivery of the composition may limited to only one nostril or both nostrils of each bird. The nostril or nostrils to which the selected dosages are delivered may be isolated from fluid communication with ambient atmosphere during the delivery process. The isolation may be provided by a conformable seal. The beak of the bird may be restrained in a closed position during delivery of the composition.

33 Claims, 3 Drawing Sheets

U.S. PATENT DOCUMENTS

| | | | | | |
|---|---|---|---|---|---|
| 5,312,353 | A | | 5/1994 | Boggess et al. | |
| 5,318,413 | A | | 6/1994 | Bertoncini | |
| 5,429,600 | A | * | 7/1995 | Heinke | 604/516 |
| 5,538,405 | A | | 7/1996 | Patno et al. | |
| 5,651,731 | A | | 7/1997 | Gorans et al. | |
| 5,666,948 | A | * | 9/1997 | Matson | 128/200.23 |
| 5,674,052 | A | | 10/1997 | Berra | |
| 5,846,061 | A | | 12/1998 | Ledebuhr et al. | |
| 6,321,942 | B1 | * | 11/2001 | Krampen et al. | 222/82 |
| 6,396,938 | B1 | | 5/2002 | Tao et al. | |
| 6,565,533 | B1 | | 5/2003 | Smith et al. | |
| 6,585,499 | B2 | | 7/2003 | Nguyen et al. | |
| 6,634,319 | B1 | * | 10/2003 | Zermoglio et al. | 119/713 |
| 6,910,446 | B2 | * | 6/2005 | Johnston, Jr. | 119/651 |
| 2004/0143278 | A1 | * | 7/2004 | Gorans et al. | 606/164 |

* cited by examiner

APPARATUS AND METHOD FOR NASAL DELIVERY OF COMPOSITIONS TO BIRDS

BACKGROUND

Birds raised for commercial reasons (e.g., chickens, turkeys, geese, guinea fowl, ducks, etc.) are often vaccinated to treat and/or prevent infections, disease, etc. Apparatus and methods for administering vaccine to large numbers of birds are described in a variety of patent documents such as U.S. Pat. No. 4,449,968 (Peterson); U.S. Pat. No. 4,850,997 (DuBose); U.S. Pat. No. 4,177,810 (Gourlandt); U.S. Pat. No. 5,312,353 (Boggess et al.); U.S. Pat. No. 6,565,533 B1 (Smith et al.).

Many of the apparatus and methods described in these documents rely on injection (e.g., subcutaneous, intramuscular, etc.) of the vaccine. Injection of vaccines is desirable because of the ability to deliver known, controllable dosage amounts to each bird. Injection delivery does, however, have a number of disadvantages. For example, cross-contamination between birds can be an issue if the same injection device (e.g., needle, etc.) is used for multiple birds. A potentially larger issue is the cost required to accurately deliver the injection, i.e., each bird must typically be individually restrained to ensure accurate delivery of the desired dose. Restraint can also be important to reduce the chance that the type of injection (e.g., subcutaneous, intramuscular, etc.) is improperly performed. In spite of such measures, however, birds can, e.g., receive an intramuscular injection when a subcutaneous injection is desired or vice versa. Such misdelivery of vaccines can negatively impact their efficacy.

One approach to addressing the problems associated with injection delivery methods is the use of spray equipment to deliver vaccines to groups of birds (U.S. Pat. No. 4,449,968 (Peterson); U.S. Pat. No. 4,850,997 (DuBose)). Such an approach has a number of drawbacks such as, e.g., the inability to accurately control dosage to each bird, misdelivery of vaccines (e.g., where the vaccine is inhaled when inhalation is not desired), excessive waste (for the vaccine that is not delivered to any bird, etc.).

Another approach to the vaccine delivery problem involves the use of a dropper to deliver a vaccine-laden drop into the eye of a bird restrained for other purposes (e.g., debeaking, etc.). This approach raised problems such as accuracy in the dosage delivered (e.g., if the drop missed the bird's eye due to anatomical variations, etc.), speed of the delivery (e.g., premature release of the bird may result in loss of significant amounts of the vaccine before it is irreversibly delivered to the bird), etc.

Another approach to vaccine delivery involves spraying vaccine into the mouth of a bird when restrained for another purpose (e.g., debeaking, etc.). Problems encountered with this approach included secondary bacterial infections in the lungs (potentially leading to death), and the incompatibility of many vaccines with oral delivery.

SUMMARY OF THE INVENTION

The present invention provides apparatus and methods for delivering a composition to a bird. A selected dosage of the composition is preferably delivered directly to one or both nostrils of the bird. The deliveries are performed through one or two fluid passages that are preferably in direct fluid communication with the birds' nostrils. Delivery of the composition may limited to only one nostril or both nostrils of each bird.

In various embodiments, the nostril or nostrils to which the selected dosages are delivered may preferably be isolated from fluid communication with ambient atmosphere during the delivery process. The isolation may be provided by a conformable seal. In some embodiments, the beak of the bird may be restrained in a closed position during delivery of the composition.

Among the potential advantages of the apparatus and methods of the present invention is the ability to accurately deliver selected dosages to each bird. That ability is made possible because the fluid passages through which the selected dosages are in direct fluid communication with at least one nostril of the bird.

Accuracy in the delivery process may be further enhanced if the nostril is isolated from fluid communication with ambient atmosphere. That isolation may preferably involve sealing the junction between the delivery opening of each fluid passage and one or both nostrils of a bird. The sealing may be performed by, e.g., a conformable seal located proximate the delivery opening.

Another potential advantage of the apparatus and methods of the present invention is in higher utilization of the vaccine as compared to, e.g., systems in which one or more birds are sprayed with a composition through a device that is not in direct fluid communication with one or more nostrils of each bird. In most instances, substantially all of the composition exiting the delivery opening of a fluid passage is communicated into the nostril of the subject bird (although minor amounts may be located on the beak surface proximate the nostril).

As used in connection with the present invention, the phrase "direct fluid communication" means that fluids moving through a fluid passage and exiting the delivery opening of the fluid passage are transmitted directly into the nostril or nostrils of the bird. It may be preferred that, e.g., "direct fluid communication" be established by locating the delivery opening of the passage be located within 5 millimeters (mm) or less from a nostril. Thus, "direct fluid communication" can be distinguished from systems in which a spray nozzle or head is positioned to spray a composition in the direction of the bird where it can fall onto the bird's feathers, eyes, or be inhaled.

Another potential advantage of the apparatus and methods of the present invention may be in efficiency or speed of administration. For example, the composition may be delivered in conjunction with one or more other processes being performed on a bird such as, e.g., upper beak treatment, lower beak treatment, etc. Such beak treatment processes may be described in, e.g., U.S. Pat. Nos. 5,651,731 (Gorans et al.); U.S. patent application Ser. No. 10/346,981, titled APPARATUS AND METHOD FOR UPPER AND LOWER BEAK TREATMENT, filed Jan. 17, 2003; U.S. patent application Ser. No. 10/702,369, titled BEAK TREATMENT WITH TONGUE PROTECTION, filed on Nov. 6, 2003; and U.S. patent application Ser. No. 10/702,370, titled AUTOMATED HATCHLING PROCESSING METHOD AND SYSTEM, filed on Nov. 6, 2003.

Although the composition delivery is described herein as potentially being performed in conjunction with one or more other processes, the actual delivery of composition may be accomplished before the other processes, after the other processes, in between two other processes, and/or simultaneously with one or more of the other processes.

Although the present invention is described with respect to delivery of a composition, it should be understood that the apparatus and methods may be used to deliver more than one composition to a bird, with the different compositions being potentially delivered simultaneously or sequentially. Furthermore, the apparatus and methods may be used to deliver multiple selected dosages of a composition as opposed to a single selected dosage.

In one aspect, the present invention provides a method of delivering a composition to a bird by locating a delivery opening of a fluid passage in direct fluid communication with at least one nostril of a bird; and delivering a selected dosage of a composition to the at least one nostril through the fluid passage, the dosage entering the at least one nostril after exiting the delivery opening of the fluid passage.

In another aspect, the present invention provides a method of delivering a composition to a bird by locating a delivery opening of a fluid passage in direct fluid communication with at least one nostril of a bird; delivering a selected dosage of a composition to the at least one nostril through the fluid passage, the dosage entering the at least one nostril after exiting the delivery opening of the fluid passage; isolating the at least one nostril from fluid communication with ambient atmosphere while delivering the selected dosage; and restraining the beak of the bird in a closed position while delivering the selected dosage.

In another aspect, the present invention provides an apparatus for delivering a composition to at least one nasal passage of a bird, the apparatus including a bird head positioning body comprising a beak receiving void formed therein, the beak receiving void comprising an interior surface facing a bird head located in the beak receiving void; and a passage formed in the bird head positioning body, the passage comprising a delivery opening proximate the interior surface of the beak receiving void, wherein the passage is in direct fluid communication with at least one nostril of a bird head located in the beak receiving void through the delivery opening.

In another aspect, the present invention provides an apparatus for delivering a composition to at least one nasal passage of a bird, the apparatus including a bird head positioning body having a beak receiving void formed therein, the beak receiving void including an interior surface facing a bird head located in the beak receiving void; and a pair of passages formed in the bird head positioning body, wherein each passage of the pair of passages includes a delivery opening proximate the interior surface of the beak receiving void, wherein each passage of the pair of passages is in direct fluid communication with one nostril of a bird head located in the beak receiving void through the delivery opening.

In another aspect, the present invention provides an apparatus for delivering a composition to at least one nasal passage of a bird, the apparatus including a closed fluid passage in fluid communication with at least one nostril of a bird; a source of a composition to be delivered to the bird; and means for delivering the composition to the at least one nostril of the bird through the closed fluid passage.

In another aspect, the present invention provides a method of delivering a composition to a bird by locating a delivery opening of a first fluid passage in direct fluid communication with a first nostril of a bird; locating a delivery opening of a second fluid passage in direct fluid communication with a second nostril of a bird; and delivering a first selected dosage of a composition to the first nostril through the first fluid passage, the dosage entering the first nostril after exiting the delivery opening of the first fluid passage.

These and other features and advantages of the invention may be described in more detail below with respect to illustrative embodiments of the invention.

DETAILED DESCRIPTION OF ILLUSTRATIVE EMBODIMENTS OF THE INVENTION

In the following detailed description of illustrative embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention. Furthermore, like reference numbers denote like features in the different figures.

Figure 1:
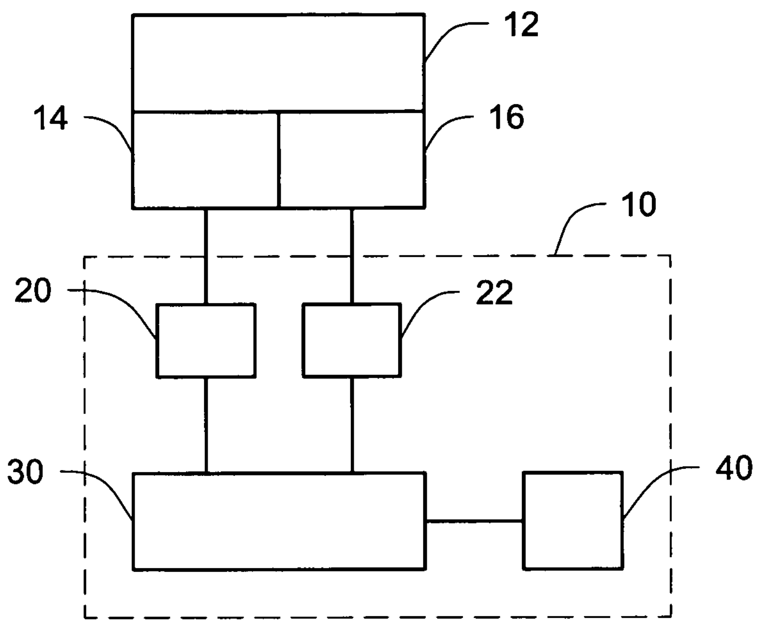
FIG. 1 is schematic diagram of one apparatus for delivering a composition to at least one nasal passage of a bird.

Referring to FIG. 1, a schematic block diagram of one system 10 for delivering a composition to a bird 12 is depicted. The bird 12 typically includes a first nostril 14 and a second nostril 16.

The depicted illustrative embodiment of system 10 includes a first fluid passage 20 and a second fluid passage 22. It may be preferred that, as depicted, the first fluid passage 20 be in direct fluid communication with only one nostril (the first nostril 14 as depicted) and that the second fluid passage 22 be in direct fluid communication with the other nostril (the second nostril 16 as depicted).

In one alternative, only one fluid passage may be provided that is in fluid communication with only one nostril (e.g., first fluid passage 20 in fluid communication with only the first nostril 14). In such an alternative, it may be desirable to block or isolate the second nostril 16 from ambient atmosphere when delivering a fluid composition to the first nostril 14.

In another alternative, a single fluid passage may be provided that is in fluid communication with both the first nostril 14 and the second nostril 16 of the bird 12. In such a system, the delivery of a composition may be to both nostrils 14 and 16 simultaneously.

The fluid passages 20 and 22 may take any suitable form or structure. One example is depicted and described below in connection with FIGS. 3 & 4. Many other variations are, however, possible. For example, the fluid passages may take the form of tubes (e.g., silicone tubes, metal tubes, etc.) or other structures.

The passages 20 and 22 may include structures that aid in desired delivery of the selected dosages of the composition. For example, the passages 20 and 22 may terminate in spray nozzles, atomizers, etc. that can affect the characteristics of the composition as delivered.

Furthermore, the passages 20 and 22 may include structures that assist in isolating the nostril or nostrils 14 and 16 to which the passages deliver composition. For example, the fluid passages 20 and 22 may include seals that are shaped to assist in isolating the bird's nostrils. The seals may preferably be made of a conformable material, e.g., foams, elastomers, etc. that can adapt to variations in the shapes of the bird's anatomy to provide the desired degree of isolation.

The system 10 includes means for delivering 30 a composition to both the first passage 20 and the second passage 22.

The means for delivering 30 may take any suitable form provided that it is capable of delivering the selected dosages of a composition to the bird 12. Examples of suitable means for delivering include positive displacement type pumps such as, e.g., syringe-type pumps, gear pumps, peristaltic pumps, pinch pumps, etc. The means for delivering may also include pumps normally adapted for continuous delivery of a fluid with the appropriate use of, e.g., valving, to allow for the dispensing of discrete selected dosages as needed. One preferred type of pump to use as the delivery means may be a pinch pump with two occluders on each end of a length of tubing.

The delivery means 30 is located in fluid communication with a source 40 of the composition to be delivered to the bird 12. The source 40 may be provided in any suitable form, e.g., a tank, vat, ampoule, bag, bladder, etc. The composition may be pre-mixed, or mixed at the source 40 as needed.

Figure 2:
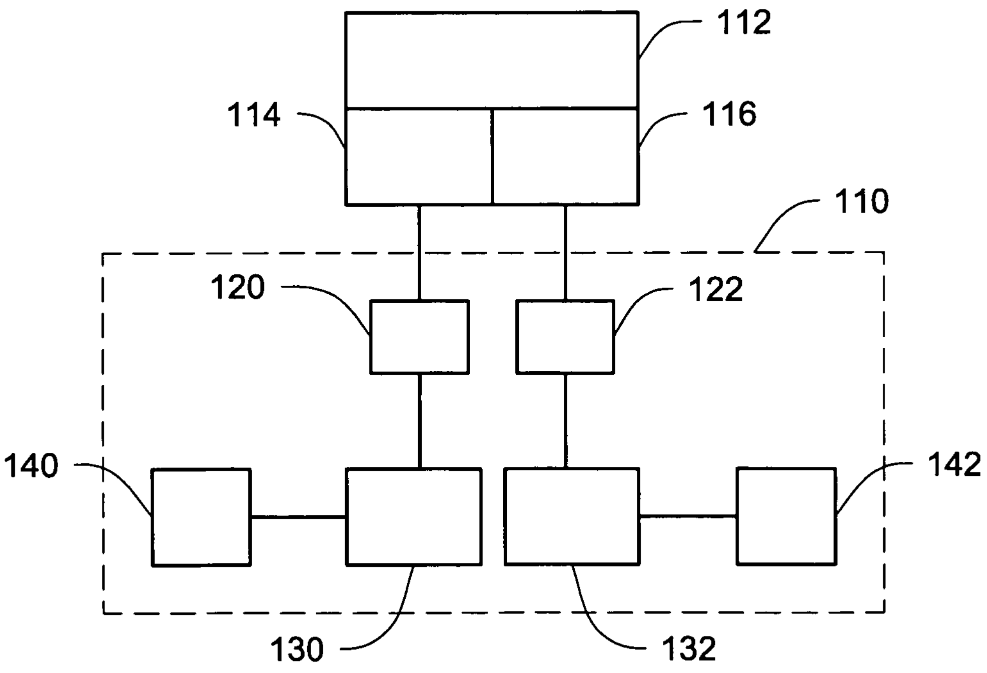
FIG. 2 is a schematic diagram of another apparatus for delivering a composition to at least one nasal passage of a bird.

FIG. 2 depicts another illustrative system 110 for delivering a selected dosage of a composition to a bird 112. The system 110 is similar in many respects to the system 10 of FIG. 1. For example, the depicted illustrative embodiment of system 110 includes a first fluid passage 120 and a second fluid passage 122. It may be preferred that, as depicted, the first fluid passage 120 be in direct fluid communication with only one nostril (the first nostril 114 as depicted) and that the second fluid passage 122 be in direct fluid communication with the other nostril (the second nostril 116 as depicted).

One difference between system 10 depicted in FIG. 1 and system 110 depicted in FIG. 2, is that each of the passages 120 and 122 is independently supplied with the compositions to be delivered to the bird 112. As seen in FIG. 2, fluid passage 120 is supplied by means for delivering a composition 130 from a source 140 while fluid passage 122 is supplied by means for delivering a composition 132 from a source 142. Both the different means 130 and 132 may preferably be independent from each other such that the associated fluid passages 120 and 122 are capable if delivering composition independent from the other.

In a system 110 configured as depicted, each passage 120 and 122 can be used to deliver different selected dosages to the different nostrils 114 and 116 of bird 112. Such delivery is possible because of the independent nature of the means for delivering 130 and 132 associated with each of the fluid passages 120 and 122. Furthermore, the dosages from each passage 120 and 122 can be delivered simultaneously or at different times as desired.

In another variation, the fluid passages 120 and 122 (and their associated means for delivering 130 and 132) may be used to deliver different compositions from the different sources 140 and 142 to the different nostrils 114 and 116 of the bird 112. The different compositions in sources 140 and 142 may different in constituents or in some other characteristic (such as, e.g., potency, etc.).

Where the compositions in sources 140 and 142 are different, the system 110 may be used to adapt to differences in the birds 112 to which the composition or compositions are to be delivered. The source 140 and 142 from which a composition is delivered may be selected based on one or more characteristics of the bird 112. For example, the system 110 may deliver compositions from different sources 140 and 142 based on, e.g., a bird's weight, gender, breed, age, etc.

Although not depicted in FIGS. 1 & 2, a system for delivering a composition to a bird could include a single fluid passage connected to multiple means for delivering a composition such that the different means for delivering could be actuated based on the composition to be delivered through the fluid passage. Such a fluid passage may be in direct fluid communication with only one or with both nostrils of a bird.

Figure 3:
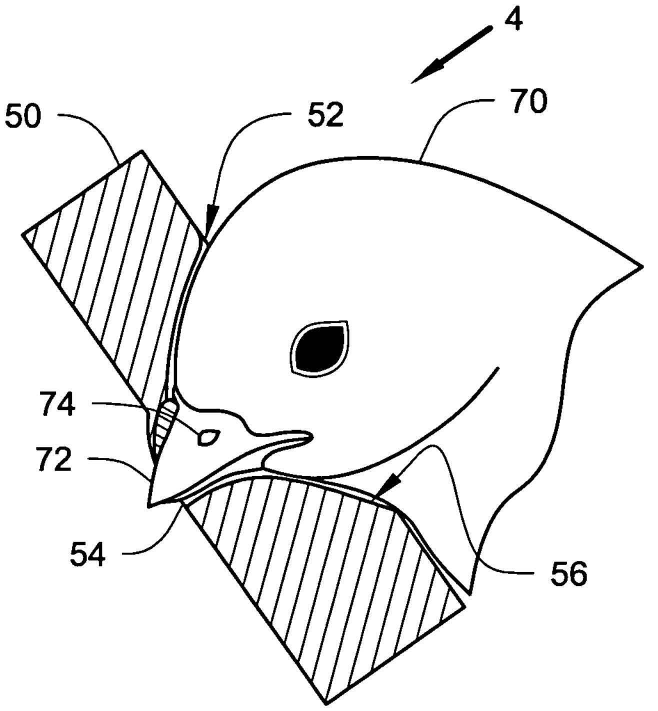
FIG. 3 is a partial cross-sectional view of one bird head positioning body useful in a system according to the present invention with a bird head located therein.
Figure 4:
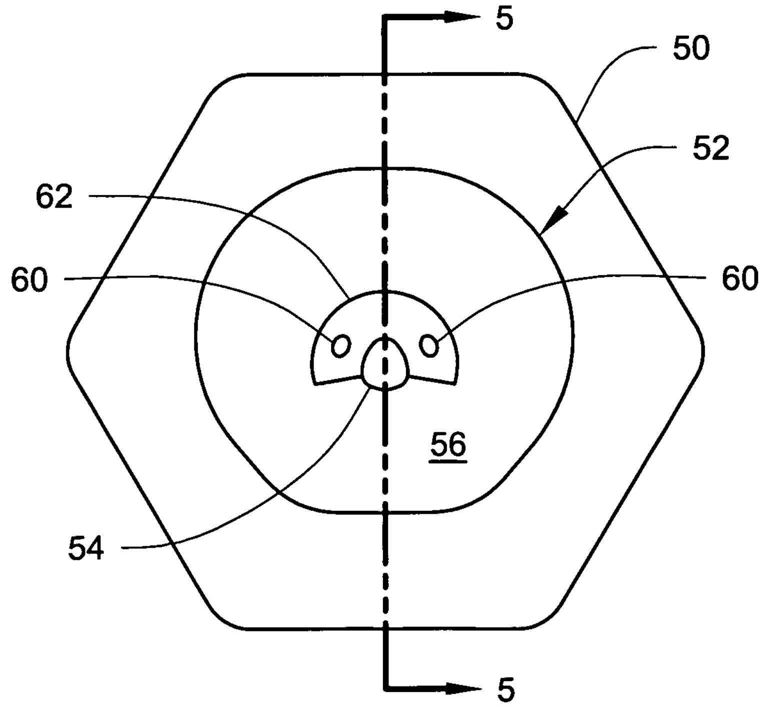
FIG. 4 is a plan view of the bird head positioning body of FIG. 3 taken along the direction of arrow 4 in FIG. 3 (with the bird head seen in FIG. 3 removed).
Figure 5:
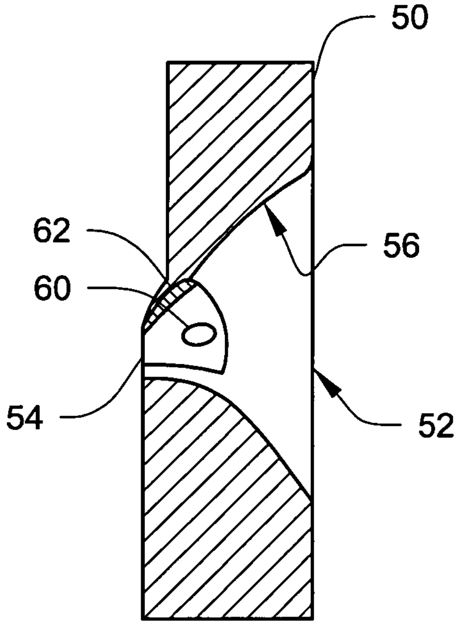
FIG. 5 is a cross-sectional view of the bird head positioning body of FIGS. 3 & 4 taken along line 5-5 in FIG. 4.

Turning now to FIGS. 3-5, one embodiment of an illustrative bird head positioning body that could be used in a system for delivering a composition to a bird is depicted. Not depicted in connection with the bird head positioning body of FIGS. 3-5 are other components of the system such as, e.g., any pump or other means of delivering the composition, a source of the composition, etc.

The depicted fixture 50 of the bird head positioning body includes a beak receiving void 52 sized to receive at least a portion of the beak 72 of a bird 70. The beak 72 includes two nostrils 74 (although only one is depicted in FIG. 3 due to the nature of the view). It may be preferred that, as seen in FIG. 3, the beak receiving void 52 be large enough such that the beak 72 of bird 70 extends through the fixture 50 until it partially protrudes from an opening 54 in the fixture 50.

The beak receiving void 52 is defined within the fixture 50 by an interior surface 56. The interior surface 56 faces the head of the bird 70 when the bird's head is located within the beak receiving void 52. The beak receiving void 52 and its interior surface 56 may preferably be shaped to conform to the shape of an average bird 70 to be processed using the fixture 50. For example, the shape may vary based on the breed, species, age, etc. of the birds to be used with the system. Although not depicted, the fixture 50 may include a pair of rotating arms or other structures to retain the head of the bird 70 within the beak receiving void 52. One example of rotating arms used in connection with a similar fixture is described in U.S. Pat. No. 5,651,731 (Gorans et al.) (where the arms are referred to as "skin bunchers").

FIG. 4 is a plan view of the fixture 50 taken along the direction of arrow 4 in FIG. 3 with the bird 70 removed so that the features are not obscured in FIG. 4. FIG. 5 is a cross-sectional view of the fixture 50 taken along line 5-5 in FIG. 4. The interior surface 56 of the beak receiving void 52 and the opening 54 are depicted in FIGS. 4 & 5. Also seen in FIG. 4 are two delivery openings 60 formed in the interior surface 56 of the fixture 50. Only one of the delivery openings 60 is depicted in FIG. 5 because of the cross-sectional view.

The delivery openings 60 are located at the ends of fluid passages through which a composition can be delivered to the bird. In the depicted fixture 50, the delivery openings 60 are located in a seal insert 62 provided in the fixture 50. The seal insert 62 may preferably be made of a conformable material such as, e.g., silicone, rubber, resilient foams, etc. If the seal insert 62 is made of conformable material, it may be deformed slightly as the beak 72 of the bird 70 (see FIG. 3) is held within the beak receiving void 52. That deformation and the result conformance can help to isolate the bird's nostrils 74 from ambient atmosphere.

The depicted seal insert 62 includes separate delivery openings 60 (one for each nostril 74 of the bird 70). In some embodiments, a seal insert may include only one delivery opening 60 that is designed to seal around only one nostril 74. In other alternative embodiments, a seal insert 62 may include a single larger delivery designed to seal around both of the bird's nostrils 74 at the same time and allow for fluid communication with both nostrils at the same time.

The fixture 50 and the seal insert 62 described herein may collectively be referred to as the bird head positioning body. In some systems, the bird head positioning body may be a unitary item molded or otherwise formed as a single body, i.e., the bird head positioning body does not require separate components for the fixture and seal insert.

The fluid passage or passages that terminate in delivery openings 60 may preferably be formed as bores through the seal insert 62 and, potentially, through the body of the fixture 50 in which the seal insert 62 is located. If a separate passage is provided for each of the delivery openings 60, it may be preferred that the passages be independent of each other as described above in connection with the systems depicted schematically in FIGS. 1 & 2.

In another alternative to a bore formed through the seal insert 62 and/or the fixture 50, the fluid passage used to deliver a composition to the nostrils 74 of the bird 70 may be formed as a groove or channel that is closed at least partially by the bird's beak 72 when the bird 70 is in position in the fixture 50. Many other variations for the actual structure of the fluid passage may also be used, e.g., a bore terminating in a groove, a wicking member or material in contact with the nostril or beak structure of the bird (such that delivery may be effected by wicking), etc.

If the bird 70 is to restrained within the fixture 50 for relatively long periods of time and if both nostrils 74 of the bird 70 are isolated by the seal insert 62, it may be desirable to allow the bird 70 to breathe through the delivery openings 60.

Another optional feature of the present invention depicted in connection with the fixture of FIGS. 3-5 is that the beak receiving void 52 and the opening 54 may preferably be sized to restrain the beak 72 of the bird 70 closed. Restraint of the beak 72 in a closed position may assist in the delivery of any selected dosages of a composition to, e.g., the nasal passages of the bird 70 by reducing or preventing the composition from escaping through an open beak during delivery.

As noted above, the opening 54 in the fixture 50 may prefereably be sized to allow a portion of the bird's beak 72 to protrude from the fixture 50. Such an arrangement may be useful if the fixture 50 is to have multiple uses. For example, the fixture 50 may also be used to restrain the bird 70 during beak treatment processes such as those described in, e.g., U.S. Pat. No. 5,651,731 (Gorans et al.); U.S. patent application Ser. No. 10/346,981, titled APPARATUS AND METHOD FOR UPPER AND LOWER BEAK TREATMENT, filed Jan. 17, 2003; and U.S. patent application Ser. No. 10/702,369, titled BEAK TREATMENT WITH TONGUE PROTECTION, filed on Nov. 6, 2003.

The fixture 50 may also serve as, e.g., a hatchling carrier that can be used to restrain a hatchling during multiple processes such as, e.g., beak treatments, weighing, cleaning, sexing, etc. Examples of some processing systems and methods in which such a hatchling carrier may be used are described in U.S. patent application Ser. No. 10/702,370, titled AUTOMATED HATCHLING PROCESSING METHOD AND SYSTEM, filed on Nov. 6, 2003.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

The invention claimed is:

1. An apparatus for delivering a composition to at least one nasal passage of a bird, the apparatus comprising:

a bird head positioning body that comprises a first major side, a second major side, and a beak receiving void formed through the first and second major sides of the bird head positioning body, wherein the beak receiving void defines an opening in the first major side of the bird head positioning body and an opening in the second major side of the bird head positioning body, and further wherein the beak receiving void defines a cavity in the bird head positioning body that extends from the opening in the first major side to the opening in the second major side, and wherein at least a portion of a beak of a bird head located in the beak receiving void protrudes through the opening in the second major side of the bird head positioning body and is exposed proximate the second major side of the bird head positioning body, the beak receiving void comprising an interior surface facing a bird head located in the beak receiving void; and a passage formed through the bird head positioning body, the passage comprising a delivery opening in the interior surface of the beak receiving void, wherein the passage is positioned to be in direct fluid communication with at least one nostril of a bird head located in the beak receiving void through the delivery opening.

2. An apparatus according to claim 1, wherein the passage further comprises a conformable seal proximate the delivery opening, wherein the conformable seal isolates the at least one nostril of a bird head located in the beak receiving void.

3. An apparatus according to claim 1, wherein the passage comprises a bore formed through the bird head positioning body.

4. An apparatus according to claim 1, further comprising means for delivering a composition to the at least one nostril of a bird head located in the beak receiving void, wherein the means for delivering is in fluid communication with the passage in the bird head positioning body.

5. An apparatus according to claim 1, further comprising a pump in fluid communication with the passage in the bird head positioning body.

6. An apparatus for delivering a composition to at least one nasal passage of a bird, the apparatus comprising:

a bird head positioning body that comprises a first major side, a second major side, and a beak receiving void formed through the first and second major sides of the bird head positioning body, wherein the beak receiving void defines an opening in the first major side of the bird head positioning body and an opening in the second major side of the bird head positioning body, and further wherein the beak receiving void defines a cavity in the bird head positioning body that extends from the opening in the first major side to the opening in the second major side, and wherein at least a portion of a beak of a bird head located in the beak receiving void protrudes through the opening in the second major side of the bird head positioning body and is exposed proximate the second major side of the bird head positioning body, the beak receiving void comprising an interior surface facing a bird head located in the beak receiving void; and a pair of passages formed through the bird head positioning body, wherein each passage of the pair of passages comprises a delivery opening in the interior surface of the beak receiving void, wherein each passage of the pair of passages is positioned to be in direct fluid communication with one nostril of a bird head located in the beak receiving void through the delivery opening.

7. An apparatus according to claim 6, wherein each passage of the pair of passages is independent such that delivery of fluids through the passages to each of the nostrils of a bird head located in the beak receiving void can be independently controlled.

8. An apparatus according to claim 6, wherein each passage further comprises a conformable seal proximate the delivery opening of the passage.

9. An apparatus according to claim 8, wherein each conformable seal isolates one nostril of a bird head located in the beak receiving void.

10. An apparatus according to claim 6, wherein each passage comprises a bore formed through the bird head positioning body.

11. An apparatus according to claim 10, wherein the bore and the delivery opening of each passage of the pair of passages are independent of each other such that delivery of fluids through the passages to each of the nostrils of a bird head located in the beak receiving void can be independently controlled.

12. An apparatus according to claim 6, further comprising means for delivering a composition, wherein the means for delivering is in fluid communication with at least one passage of the pair of passages in the bird head positioning body.

13. An apparatus according to claim 6, further comprising a pump in fluid communication with at least one passage of the pair of passages in the bird head positioning body.

14. An apparatus for delivering a composition to at least one nasal passage of a bird, the apparatus comprising:

a bird head positioning body comprising a beak receiving cavity formed through the bird head positioning body, the beak receiving cavity being bounded within the bird head positioning body by a continuous interior surface that defines the shape of the beak receiving cavity within the bird head positioning body;

a passage formed through the bird head positioning body, wherein the passage terminates at a delivery opening formed in the interior surface of the beak receiving cavity, wherein a conformable seal is located proximate the delivery opening, and wherein the passage is positioned to be in direct fluid communication with one nasal passage in a beak through the delivery opening when the beak is located in the beak receiving cavity.

15. An apparatus according to claim 14, wherein the bird head positioning body comprises a unitary item formed as a single body.

16. An apparatus according to claim 14, further comprising means for delivering a fluid composition to the delivery opening through the passage in the bird head positioning body.

17. An apparatus according to claim 14, further comprising a pump in fluid communication with the passage in the bird head positioning body.

18. An apparatus for delivering a composition to at least one nasal passage through a nostril of a bird comprising a beak, the apparatus comprising:

a bird head positioning body comprising a beak receiving cavity formed therein, the beak receiving cavity comprising an interior surface sized to restrain closed a beak of a bird when the beak is located in the beak receiving cavity;

a passage formed through the bird head positioning body, wherein the passage terminates at a delivery opening formed in the interior surface of the beak receiving cavity, wherein the passage is positioned to be in direct fluid communication with one nasal passage in a beak through the delivery opening when the beak is located in the beak receiving cavity.

19. An apparatus according to claim 18, wherein the bird head positioning body comprises a unitary item formed as a single body.

20. An apparatus according to claim 18, further comprising means for delivering a fluid composition to the delivery opening through the passage in the bird head positioning body.

21. An apparatus according to claim 18, further comprising a pump in fluid communication with the passage in the bird head positioning body.

22. An apparatus for delivering a composition to at least one nasal passage of a bird, the apparatus comprising:

a bird head positioning body that comprises a first major side and a second major side and a thickness between the first and second major sides;

a beak receiving cavity formed through the bird head positioning body, wherein the beak receiving cavity comprises:

a first opening in the first major side of the bird head positioning body;

a second opening in the second major side of the bird head positioning body;

an inner surface that extends from the first opening in the first major side to the second opening in the second major side of the bird head positioning body, wherein the inner surface faces the beak receiving cavity and extends around a perimeter of the beak receiving cavity such that the inner surface defines the shape of the beak receiving cavity between the first major side and the second major side of the bird head positioning body; and a passage formed through the bird head positioning body, the passage comprising a delivery opening in the inner surface of the beak receiving cavity, wherein the passage is adapted to be in direct fluid communication with one nasal passage in a beak through the delivery opening when a beak is located in the beak receiving cavity.

23. An apparatus according to claim 22, wherein the passage further comprises a conformable seal proximate the delivery opening.

24. An apparatus according to claim 22, wherein the bird head positioning body comprises a unitary item formed as a single body.

25. An apparatus according to claim 22, further comprising means for delivering a fluid composition to the delivery opening through the passage in the bird head positioning body.

26. An apparatus according to claim 22, further comprising a pump in fluid communication with the passage in the bird head positioning body.

27. An apparatus according to claim 22, wherein the second opening in the second major side is sized to retain a beak inserted through the second opening closed.

28. An apparatus according to claim 22, wherein the inner surface comprises a continuous inner surface that extends completely around the perimeter of the bird receiving cavity.

29. An apparatus for delivering a composition to at least one nasal passage of a bird, the apparatus comprising:

a bird head positioning body that comprises a first major side and a second major side;

a beak receiving cavity formed through the first and second major sides of the bird head positioning body, wherein the beak receiving cavity comprises:

a first opening in the first major side of the bird head positioning body;

a second opening in the second major side of the bird head positioning body;

an inner surface that extends from the first opening in the first major side to the second opening in the second major side of the bird head positioning body, wherein the inner surface faces the beak receiving cavity and extends completely and continuously around a perimeter of the beak receiving cavity between the first major side and the second major side, wherein the inner surface defines the shape of the beak receiving cavity between the first major side and the second major side of the bird head positioning body; and at least one passage formed through the bird head positioning body, the at least one passage comprising a delivery opening in the inner surface of the beak receiving cavity, wherein the at least one passage is adapted to be in direct fluid communication with at least one nasal passage in a beak through the delivery opening when a beak is located in the beak receiving cavity.

30. An apparatus according to claim 29, wherein the at least one passage comprises a pair of passages.

31. An apparatus according to claim 29, wherein the at least one passage further comprises a conformable seal proximate the delivery opening.

32. An apparatus according to claim 29, wherein the bird head positioning body comprises a unitary item formed as a single body.

33. An apparatus according to claim 29, wherein the second opening in the second major side is sized to retain a beak inserted through the second opening closed.

* * * * *